United States Patent [19]

Nelson

[11] Patent Number: 5,681,712
[45] Date of Patent: Oct. 28, 1997

[54] SURFACE COLONY COUNTING DEVICE AND METHOD OF USE

[75] Inventor: Robert L. Nelson, Bloomington, Minn.

[73] Assignee: Minnesota Mining and Manufacturing Company, St. Paul, Minn.

[21] Appl. No.: 457,346

[22] Filed: Jun. 2, 1995

[51] Int. Cl.$^6$ .................................................. C12Q 1/24
[52] U.S. Cl. .................. 435/30; 435/29; 435/34; 435/39; 435/308.1; 435/810
[58] Field of Search .................. 435/305.1, 305.4, 435/288.3, 308.1, 297.5, 810, 29, 30, 34, 39; 422/57, 60, 61

[56] References Cited

U.S. PATENT DOCUMENTS

| | | | |
|---|---|---|---|
| 3,929,583 | 12/1975 | Sharpe et al. | 435/288.5 |
| 4,335,206 | 6/1982 | Wilkins et al. | 435/288.3 |
| 4,565,783 | 1/1986 | Hansen et al. | 435/299 |
| 5,089,413 | 2/1992 | Nelson et al. | 435/254 |
| 5,137,812 | 8/1992 | Matner | 435/38 |
| 5,210,022 | 5/1993 | Roth et al. | 435/34 |
| 5,232,838 | 8/1993 | Nelson et al. | 435/30 |
| 5,360,722 | 11/1994 | Inoue et al. | 435/24 |
| 5,364,766 | 11/1994 | Mach et al. | 435/34 |
| 5,409,838 | 4/1995 | Wickert | 435/288.3 |
| 5,424,122 | 6/1995 | Crandall et al. | 428/355 |

FOREIGN PATENT DOCUMENTS

WO 92/07899 5/1992 WIPO.

*Primary Examiner*—Donald E. Czaja
*Assistant Examiner*—Lien Tran
*Attorney, Agent, or Firm*—Gary L. Griswold; Walter N. Kirn; James A. Rogers

[57] ABSTRACT

A thin film culture plate device having a body member including a self-supporting substrate coated on its upper surface with a layer of an adhesive composition and a layer of cold-water-soluble powder and having an apertured spacer member attached to the upper surface of the substrate. These thin film culture plate devices may also include an optional cover sheet, covering at least a portion of the apertured spacer member. Kits including microorganism filters and/or packages containing nutrient mixtures and/or selective agents are described.

6 Claims, 1 Drawing Sheet

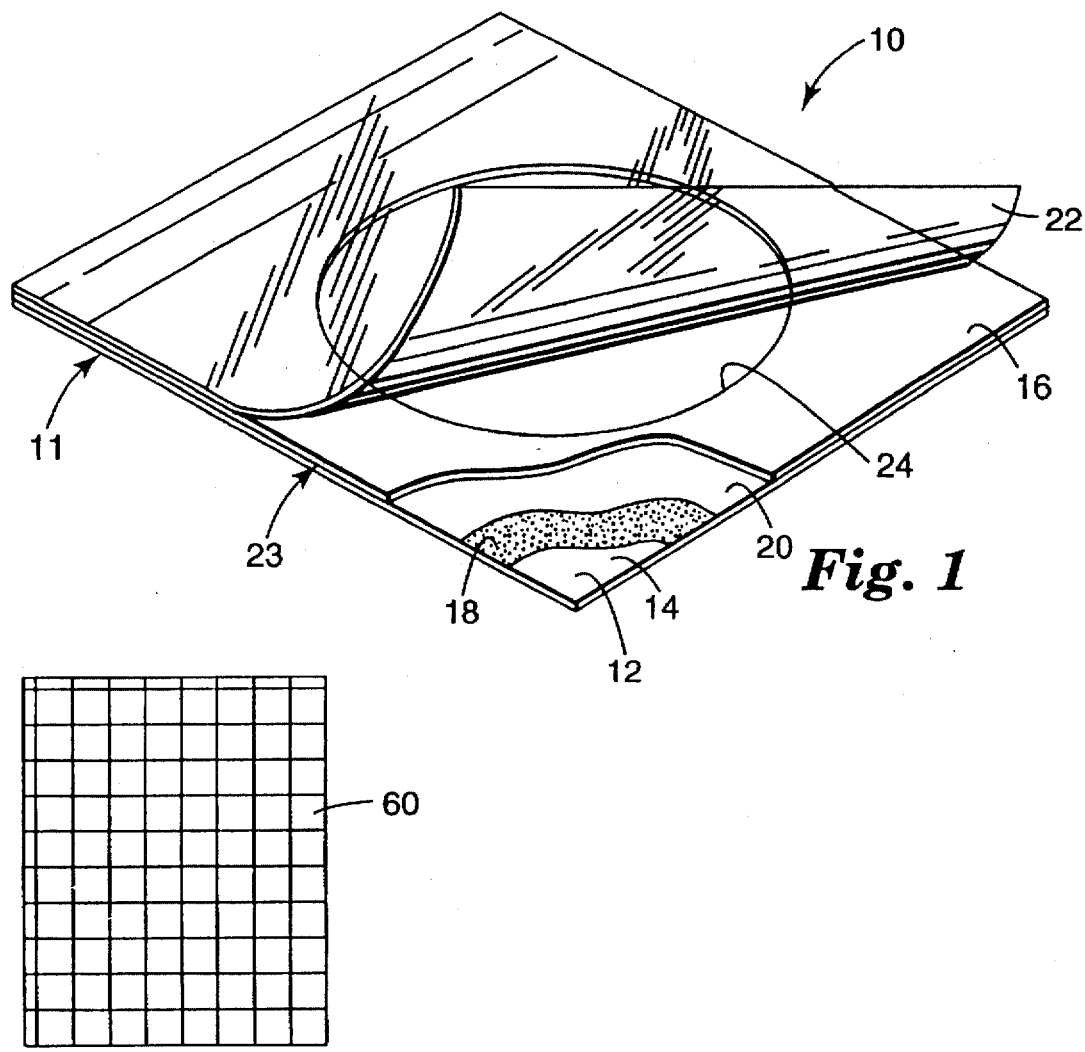
Fig. 1
Fig. 2
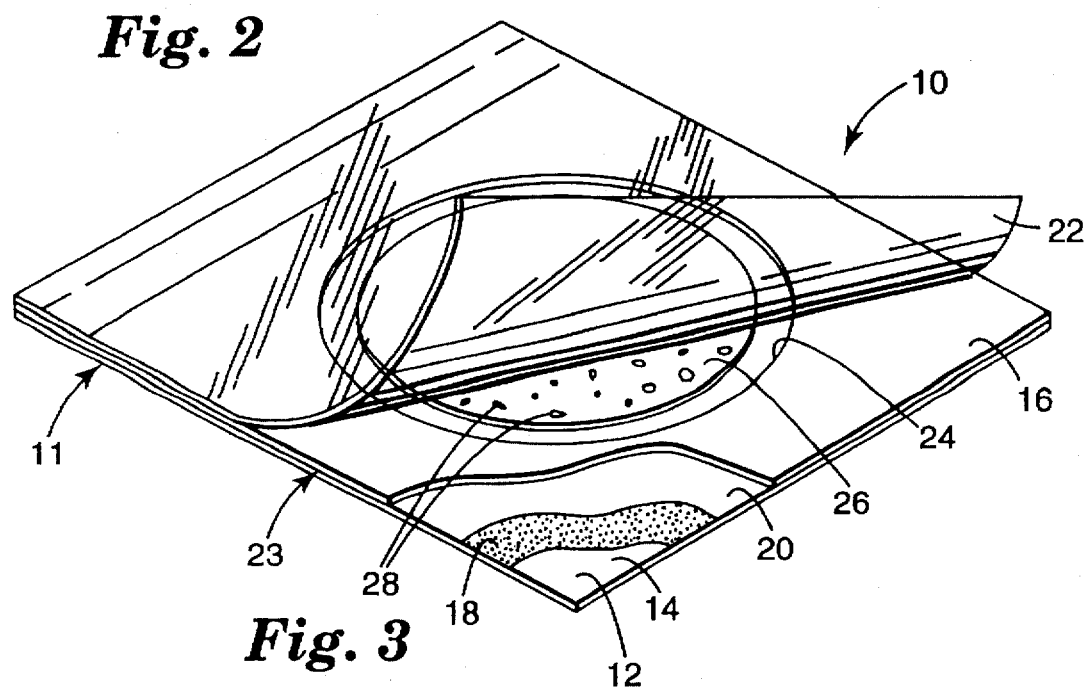
Fig. 3

SURFACE COLONY COUNTING DEVICE AND METHOD OF USE

The present invention relates to methods and devices for growing, detecting and/or enumerating microorganisms. More particularly, this invention relates to methods, devices and kits for growing, detecting and/or enumerating microorganisms which are either present in a liquid sample or present on the surface of a membrane such as a microbial filter.

BACKGROUND

A variety of methods and processes are currently available to determine, identify and enumerate microorganisms in different types of samples. These methods include the traditional agar plate methods, a variety of recently developed immunochemical methods and the well known PETRIFILM thin film culture plate devices.

PETRIFILM culture plate devices include devices described in U.S. Pat. No. 4,565,783 as well as variations of these devices such as those described in U.S. Pat. Nos. 5,137,812 and 5,232,838. These devices are convenient and relatively inexpensive and rapid to use. A common feature of commercially available devices is the inoculation of a liquid sample to be evaluated for the presence of microorganisms into a nutrient containing medium. Indicators may be present in the medium or may be added, for example, from the cover sheet of such devices. The cover sheet is generally placed in direct contact with the inoculated medium and the microorganisms are grown Under appropriate conditions. However, for some purposes it would be advantageous that the growing microorganisms be placed and grown without the direct contact of the cover sheet.

The present invention addresses the difficulties presented in attempting to grow, detect and enumerate microorganisms contained within a culture medium which is bonded to an adhesive.

SUMMARY OF THE INVENTION

This invention provides methods, devices and kits for growing, detecting and/or enumerating microorganisms in a sample, which microorganisms are optionally presented on the surface of a membrane such as a microbial filter. One method includes the steps of (a) adding water to a thin film culture plate device comprising a i) body member including a self-supporting substrate with upper and lower surfaces, and a layer of an adhesive composition coated on the upper surface of the substrate, wherein the adhesive composition comprises a water-insoluble adhesive, a non-inhibitory emulsifying agent, and at least one hydrophilic agent selected from the group consisting of a nutrient for growing microorganisms, a selective agent, and combinations thereof, and a cold-water-soluble powder comprising at least one gelling agent and ii) a spacer containing an aperture which is attached to the upper surface of the substrate in the aperture space (b) inserting a membrane to be evaluated for the presence of microorganisms into the aperture space onto the aqueous sample;

(c) incubating the device for a period of time; and (d) counting the number of microorganism colonies growing in the aperture space or in the space on the surface of the membrane. Alternatively, this method further includes the step of at least partially covering the aperture space of the device with a cover sheet after step (b). In another method a liquid sample is added directly to the aperature space and no membrane is used.

The devices of the invention include a surface colony counting thin film culture plate device comprising:

(a) a body member comprising a self-supporting substrate with upper and lower surfaces;

(b) a layer of a water-based adhesive composition coated on the upper surface of the substrate, wherein the water-based adhesive composition comprises a water-insoluble adhesive, a non-inhibitory emulsifying agent, and at least one hydrophilic agent selected from the group consisting of a nutrient for growing microorganisms, a selective agent, and combinations thereof; and (c) cold-water-soluble powder comprising at least one gelling agent adhered uniformly to the layer of the water-based adhesive composition; and (d) a water-insoluble spacer containing an aperture which spacer is attached to the upper surface of the substrate. The device of the invention also may include a cover sheet which partially or completely covers said aperture. The device of invention may also further comprise a membrane, such as a microbial filter, that fits within the aperture of the spacer.

The cover sheet, when present, is optionally transparent.

The present invention provides both a method and thin film culture plate device which readily allows growth, detection and enumeration of microorganisms on the surface of a membrane or microbial filter. The present invention further enables the detection of coliform bacteria with reduced interference of tiny entrapped gas bubbles.

Although the method and device of the present invention are particularly suited for counting surface colonies, they may also be used when it is desired to minimize the contact of a cover sheet with the colonies to be counted.

The present invention also provides novel kits for the growth, detection and enumeration of microorganisms. These kits contain thin film culture plate devices of this invention and one or more additional components. The additional components are microbial filters and/or packages including hydrophilic agents. The packages including hydrophilic agents may include one or more nutrients for growing microorganisms, selective agents and/or carrier systems.

These and various other advantages and features which characterize the invention are pointed out with particularity in the claims. However, for a better understanding of the invention, its advantages, and objects obtained by its use, reference should be had to the Drawing and to the accompanying descriptive matter, in which there is illustrated and described preferred embodiments of the invention.

BRIEF DESCRIPTION OF THE DRAWING

The invention may be further illustrated by reference to the accompanying drawing wherein:

FIG. 1 is a top perspective view, partially in section, of an embodiment of a thin film culture plate device;

FIG. 2 is a top view of the thin film culture plate device of FIG. 1 showing a grid pattern printed on a body member of the culture media device; and FIG. 3 is a top perspective view, partially in section, of another embodiment of a thin film culture plate device.

DETAILED DESCRIPTION OF EMBODIMENTS OF THE INVENTION

Definitions

For the purposes of this invention,

"liquid sample" refers to an aqueous mixture, including food samples that are homogenized, diluted, or suspended in the aqueous mixture, that can contain various microorganisms therein;

"powder" refers to particulate material of one or more gelling agents having an average diameter suitable for use in the thin film culture plate device(s) of the present invention, preferably a diameter of about 10–400 microns more preferably a diameter of about 30–90 microns.

"cold-water-soluble powder" refers to a powder that forms a gel in room temperature water (e.g., about 18° C. to 24° C.) when combined with an aqueous test sample;

"non-inhibitory emulsifying agent" refers to an emulsifying agent, preferably a nonionic emulsifying agent, which is suitable to disperse a water-insoluble adhesive in an aqueous environment and does not substantially inhibit the growth of the microorganisms intended to be grown;

"reconstituted medium" refers to a solution or gel formed from the reconstitution of a cold-water-soluble powder with water or an aqueous test sample;

"air-permeable" refers to a material which, when substantially exposed at its edges to air, is sufficiently permeable to air in the horizontal direction (i.e., parallel to its top and bottom surfaces) to provide an adequate supply of air to an overlying reconstituted medium in order to support the growth of aerobic microorganisms in the reconstituted medium;

"water-insoluble adhesive" refers to a hydrophobic adhesive which is substantially insoluble in an aqueous environment and preferably formed by aqueous emulsion polymerization techniques;

"water-based adhesive composition" refers to an adhesive composition of a water-insoluble adhesive which is dispersed in an aqueous environment by a non-inhibitory emulsifying agent prior to coating onto a substrate;

"substantially impermeable to microorganisms and water vapor" refers to a cover sheet which prevents undesired contamination and hydration of the underlying layers of the water-based adhesive composition and cold-water-soluble powder during shipping, storage, and use of thin film culture plate device(s), and avoids desiccation of the reconstituted medium, such that the reconstituted medium is suitable to support the growth of microorganisms during an incubation period; and "selective agent" refers to any element, compound, or composition that functions to inhibit the growth, and/or facilitate the identification, of microorganisms grown on the culture media device(s) according to the present invention.

Thin Film Culture Plate Devices

FIG. 1 illustrates a thin film culture plate device 10 in accordance with the present invention. Culture plate device 10 includes body member 11 comprising self-supporting substrate 12 having upper and lower surfaces 14 and 16, respectively. Substrate 12 is coated on its upper surface 14 with a layer of adhesive composition 18. Cold-water-soluble powder, comprising one or more gelling agents, is adhered in a thin, relatively uniform layer 20 to the adhesive composition 18. Once inoculated with an aqueous test sample (not shown), the layer of cold-water-soluble powder 20 quickly hydrates to form a reconstituted medium (not shown), which in turn is capable of growing microorganisms present either in a liquid inoculum or on the surface of a membrane such as a test sample microorganism filter (see FIG. 3). Spacer 23 partially covers substrate 12 and the surface of powder 20 and contains aperture 24. In addition, thin film culture plate device 10 optionally includes cover sheet 22, to cover the reconstituted medium formed after addition of the aqueous test sample.

In an alternative embodiment illustrated in FIG. 3, device 10 includes a microorganism filter 26 in aperture 24 of spacer 23 and shows bacterial colonies 28 on the surface of filter 26.

When using thin film culture plate device 10 illustrated in FIGS. 1 or 3, an accurate count of the colonies of microorganisms present is often deskable. As illustrated in FIG. 2, the counting of colonies of microorganisms, such as bacteria, yeast or mold colonies, can be facilitated by imprinting square grid pattern 60, on substrate 12. In addition, it will also be appreciated that square grid pattern 60 could be imprinted on cover sheet 22 to aid in the counting of microorganism colonies.

Body Member

In the culture media device 10 illustrated, respectively, in FIGS. 1 and 3, body member 11 includes self-supporting substrate 12. Substrate 12 preferably comprises a relatively stiff film of a polymeric material, including without limitation, polyolefins such as polypropylene and polyethylene, polyesters, polystyrenes, or mixtures thereof. Preferably, the self-supporting substrate 12 is substantially water-proof, such that it will not substantially absorb or otherwise be affected by water. Polyester films approximately 100μ, to 180μ, thick, polypropylene films approximately 100μ, to 200μ, thick, and polystyrene films approximately 300μ, to 380μ thick have been found to work well with the present invention. Other suitable substrates include paper with a polyethylene or other substantially water-proof coating, such as "Schoeller Type MIL" photoprint paper (Schoeller, Inc., Pulaski, N.Y.). In addition, substrate 12 can be transparent, translucent, or opaque, depending on whether one wishes to view and count microorganism colonies through substrate 12.

It is possible to use air-permeable membrane layers in the devices of the present invention as described in U.S. Pat. No. 5,232,838 which is herein incorporated by reference.

Adhesive Composition

The adhesive composition preferably is a pressure-sensitive adhesive. More preferably, the adhesive is a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer comprises a lower alkyl ($C_2$ to $C_{10}$) monomer of acrylic acid, including, without limitation, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl ($C_2$ to $C_5$))(meth)acrylamides, N-methyl(meth)acrylamide, N,N-dimethyl(meth) acrylamides, or mixtures thereof. Particularly preferred water-insoluble adhesive copolymers in accordance with the present invention include a copolymer of IOA and ACM, or an aqueous emulsion suspension of a copolymer of IOA and NVP, as described in U.S. Pat. No. 5,232,838.

The adhesive composition is preferably a water-insoluble adhesive formed by aqueous emulsion polymerization. In preparing this water-insoluble adhesive via emulsion polymerization, the above-described alkyl acrylate and alkyl amide monomers and a polymerization initiator are combined according to the preferred weight ratios in an aqueous medium that includes a noninhibitory emulsifier. See e.g., U.S. Ser. No. 07/804,296, filed Dec. 9, 1991, now Pat. No. 5,424,122 Crandall et al., the disclosure of which is herein incorporated by reference.

A typical process for producing the emulsified water-based adhesive composition according to the present invention involves first preparing an aqueous solution of a nonionic emulsifier and water. A previously-prepared mixture of the alkyl acrylate and alkyl amide monomers in the desked weight ratios, and a nonionic oleophilic polymerization initiator, is then dispersed and mixed in the aqueous solution. The mixing is carried out under homogenization conditions for about one minute in order to prepare an oil-in-water emulsion.

Preferably, the alkyl acrylate and alkyl amide monomers comprise from about 20 to 60 percent by weight, and more preferably about 30 to 50 percent by weight, of the total weight of the monomers, emulsifier, polymerization initiator, and water combined. In addition, the reaction mixture can optionally contain other additives, including neutral nonionic cross-linking agents, such as 4-acryloyloxy benzophenone or 1,6-hexanediol diacrylate (HDDA), at a level of from about 0.01% to 0.5%, preferably about 0.02% to 0.1% and most preferably about 0.03% to 0.08%, by weight based on the total weight of the monomers present.

The resulting oil-in-water emulsion is heated to induction temperature and stirred under nitrogen until polymerization occurs, as signaled by a reaction exotherm. Stirring is continued, at an elevated temperature (about 50° C. to 90° C.), for about two hours, the reaction vessel is cooled to room temperature and then the polymeric product is recovered by filtration. If the resulting composition is to be coated directly, any additives such as nutrients and hydrophilic selective agents, are added with stirring. Water is added or removed to reach an appropriate coating viscosity, and the mixture is coated onto an appropriate substrate. Typically, the adhesive composition has adhesive particle diameters ranging from about 0.1 to 0.9 microns and a Brookfield viscosity of about 5 to 15 cps. In addition, appropriate adjustments to the pH of the adhesive composition are made, as needed, to insure that the water-based adhesive composition is non-inhibitory to the growth of microorganisms. Typically, the pH of the water-based adhesive composition should be maintained at a pH of about 5 to 9, more preferably at a pH of about 6 to 8.

Suitable nonionic emulsifiers include, without limitation, polyethers, such as ethylene oxide and propylene oxide condensates in general, which include straight- and branched $C_2$ and $C_{18}$ alkyl, alkylaryl and alkenyl alcohol based copolymers of ethylene oxide and propylene oxide such as the TERGITOL X series of emulsifiers (Union Carbide Co., Danbury, Conn.), block copolymers of ethylene oxide and propylene oxide such as PLURONIC and TETRONIC emulsifiers (BASF Co., Parsippany, N.J.), and TWEENS and SPANS nonionic emulsifiers (ICI, Inc., Wilmington, Del.), which denote polyoxyalkylene derivatives of sorbitan and fatty acid esters. Specific examples of nonionic emulsifiers include, but are not limited to, ethoxylated fatty alcohols, ethoxylated alkylphenols, ethoxylated fatty acids, sorbitan derivatives, sucrose esters and derivatives, ethylene oxide-propylene oxide block copolymers, fluorinated alkyl polyoxyethylene ethanols, and mixtures thereof. A preferred nonionic emulsifying agent is an octyl phenoxy poly(ethylene oxide)ethanol (e.g., ICEPAL CA-897; Rhone Poulene, Princeton, N.J.). Preferably, the nonionic emulsifier is used at a level of about 2% to 10%, more preferably about 3% to 5% and most preferably about 4%, by weight, based on the total weight of the monomers, emulsifier and polymerization initiator combined.

Preferably, the polymerization initiator used in the formation of the water-based adhesive composition comprises a nonionic oil-soluble initiator. Non-limiting examples of suitable polymerization initiators include peroxides such as benzoyl peroxide or lauroyl peroxide, as well as azo initiators, such as 2-(carbamoylazo)-isobutyronitrile (e.g., V-30 initiator; Wako Chemicals, Dallas, Tex.) or azobisisobutyronitrile (AIBN initiator; DuPont Co., Wilmington, Del.). A particularly preferred initiator is lauroyl peroxide, used at level of about 0.02% to 0.3%, more preferably about 0.05% to 0.25% and most preferably about 0.07% to 0.2%, by weight based on the total weight of the monomers.

As noted above, the water-based adhesive composition generally incorporates one or more hydrophilic agents, including nutrients, selective agents, or combinations thereof. The specific nutrients and/or selective agents used in the water-based adhesive composition may vary depending upon the particular organisms to be grown and/or to be selectively dyed or inhibited and may be readily determined by one of ordinary skill in the art. After incorporation of the hydrophilic agents and prior to coating, the pH of the water-based adhesive composition is normalized to about pH 6.5 to pH 7.5, preferably about pH 7, to help ensure that the water be maintained at a pH of about 5 to 9, more preferably at a pH of about 6 to 8.

The non-inhibitory emulsifying agent utilized in the formation of the water-insoluble adhesive, and resulting water-based adhesive composition, is preferably a nonionic emulsifying agent. Typical nonionic emulsifying agents capable of being used in the present invention are formed by the reaction of ethylene oxide with active hydrogen compounds such as phenols, alcohols, carboxylic acids, amines, and amides. These nonionic emulsifying agents also typically exhibit a hydrophilic-lipophilic balance (HLB) of about 10 to 20, preferably about 12 to 18.

Non-limiting examples of suitable nutrients include meat peptone, casein peptone, beef extract, lactose, glucose, galactose, as well as fats, minerals and vitamins. Specific examples of nutrient formulations suitable for use in the present invention include, without limitation, Violet Red Bile, Standard Methods, and Baird-Parker nutrient formulations (all commercially available from Acumedia, Inc., Baltimore, Md.).

The hydrophilic selective agents that can be incorporated into the water-based adhesive composition provide a means for selectively inhibiting or identifying microorganisms transferred to culture plate device 10 from the aqueous test sample. Suitable selective agents can include antibiotics, such as colistin methane sulfonate or nalidixic acid, for inhibition of unwanted organisms. Other suitable inhibitory selective agents include inhibitory salts, such as bile salts which, for example, can be used to selectively grow gram-negative microorganisms.

Another useful class of hydrophilic selective agents include dyes that are metabolized by, or otherwise react with, growing microorganisms, and in so doing cause the microbial colonies to be colored or fluoresce for ease of visualization and quantification. Non-limiting examples of such dyes include triphenyl tetrazolium chloride, p-tolyl tetrazolium red, tetrazolium violet, veratryl tetrazolium blue, crystal violet, neutral red, and 5-bromo-4-chloro-3-indolyl phosphate disodium salt. Particularly preferred dyes in accordance with the present invention include crystal violet, neutral red and 5-bromo-4-chloro-3-indolyl phosphate disodium salt. However, it will be appreciated that other suitable dyes can be used depending on the particular organism(s) to be identified.

After formation, the water-based adhesive composition is coated (preferably, knife-coated) onto body member 11 at a thickness that is preferably less than the diameter of the particles of the cold-water-soluble powder to be adhered to adhesive layer 18. When coating the water-based adhesive composition, the object is to apply enough adhesive composition to facilitate adherence of the powder to upper surface 14 of substrate 12, but not so much that the particles become completely embedded in the layer of water-based adhesive composition 18. Generally, a water-based adhesive composition level of about 0.20 to 0.001 $g/cm^2$, more preferably about 0.006–0.12 $g/cm^2$, and most preferably about 0.008 to 0.08 $g/cm^2$ is suitable. The layer of water-based adhesive composition 18 may then be dried, if desired, to remove remaining water before coating with the layer of cold-water-soluble powder 20.

Cold-Water-Soluble Powder

Suitable gelling agents for inclusion in the cold-water-soluble powder include both natural and synthetic gelling agents that form solutions in water at room temperature. Standard gelling agents, such as hydroxyethyl cellulose, carboxymethyl cellulose, poly-acrylamide, locust bean gum, guar gum, xanthan gum and algin, as well as super-absorbent materials, including glycol modified polysaccharides, such as UCARGEL super absorbent agents (Union Carbide, Boundbrook, N.J.), and starch-graft-poly(sodium acrylate-co-acrylamides), such as WATER LOCK super absorbent agents (Grain processing Corp., Museatine, Iowa). In particularly preferred embodiment, guar gum and xanthan gum are combined in a 1:2 weight ratio.

Preferably, the cold-water-soluble powder is a mixture of super-absorbent materials with water absorbency of about 50 ml/g to 200 ml/g, more preferably about 100 ml/g to 180 ml/g and standard gelling agents with water absorbency of about 1 ml/g to 20 ml/g, more preferably about 5 ml/g to 10 ml/g. Use of a mixture of super-absorbent materials and standard gelling agents in the cold-water-soluble powder provides a powder coating that can rapidly hydrate to contain a relatively large sample volume (e.g., at least about 5 ml) on a substrate surface area of a size which is easily handled and stored (e.g., about 75 $cm^2$), while using a relatively small amount of cold-water-soluble power (e.g., only a single layer of powder).

The gelling agent is included in the cold-water-soluble powder in a sufficient amount so that a predetermined quantity of an aqueous test sample can be applied and maintained on body member 11 without having any of the aqueous test sample run off the edge of body member 11. Preferably, sufficient gelling agent is provided so that from about 1 ml to 5 ml of an aqueous test sample, placed on powder-coated body member 11, will form a semisolid reconstituted medium. It is particularly preferred that the combination of the cold-water-soluble powder and aqueous test sample form about 5% to 15% solution, more preferably about 7% to 12% solution of the mixture. Gels such as these will allow convenient handling and stacking, and provide distinct colony identification.

In most cases, about 2.5 mg to 5 mg of cold-water-soluble powder on a surface area of 1 $cm^2$ will provide a sufficiently viscous gel when hydrated with 1 ml to 5 ml of an aqueous test sample. No mixing is required, and there is no to heat the medium or otherwise treat it to obtain the gelled reconstituted medium. The size of the cold-water-soluble powder particles can be used to control the coating weight per unit area. For example, approximately 100 mesh powder coats to a weight of about 50 mg/5 cm diameter disc and a 400 mesh powder coats to a weight of about 25 mg/5 cm diameter disc.

In some embodiments, it may be desirable to incorporate nutrients into the cold-water-soluble powder, along with the gelling agent(s). Inclusion of the nutrients is particularly useful to help facilitate the initial growth of microorganisms transferred to culture media device 10 through the aqueous test sample. Further, a dye or other reagent can also be included in the cold-water-soluble powder to further enhance the visualization of microorganism colonies.

Apertured Spacer Member

The relatively thick spacer member is a feature of the devices and the method of the invention. The spacer member is much thicker than foam spacer members previously used in PETRIFILM type devices, for example as reported in U.S. Pat. No. 5,364,766. The purpose of the previously reported foam spacers was to provide a holding well for aqueous solutions added to the device. One purpose of the thicker apertured spacer member of the present invention is to locate and protect membranes placed in the aperture of the spacer member. Another purpose of the thicker spacer member is to reduce or prevent contact by a cover sheet with the growing colonies of microorganisms.

Suitable materials for the spacer member are any solid non-inhibitory natural or synthetic substance which is readily available in sheet form but is not a microorganism growth site. Polyethylene, polypropylene, polyethylene terephthalate and polystyrene are a few examples of suitable synthetic materials. In particular, relatively inexpensive commercially available polystyrene foams and polyethylene foams are preferred, and polystyrene foam is presently most preferred. Natural substances such as cellulose sheets, metal e.g. foil sheets, wood and the like are less preferred alternatives.

The thickness of the spacer member must be sufficient to enclose the membrane and avoid or at least minimize any contact of the cover sheet with the microorganism filter. Depending upon the thickness of the membrane, the spacer should be at least about 1.3 mm thick, preferably at least 1.5 mm thick and commonly about 2 mm thick. It is usually not necessary or desirable to exceed 2 or 3 mm of spacer thickness, because excessive thickness may be wasteful of material and add unnecessary weight and bulk.

Cover Sheet

In a preferred embodiment, cover sheet 22 is affixed to one edge of body member 11. Cover sheet 22 is preferably transparent to facilitate counting of the microorganism colonies, and is substantially impermeable to both microorganisms and water vapor. Generally, cover sheet 22 will have the same properties, such as transparency and preferred water impermeability, as substrate 12. Furthermore, cover sheet 22 can have patterns imprinted thereon, such as square grid pattern 60, or a mask-edge (not shown) to aid in the counting of microorganism colonies, to provide a target for placement of the aqueous test sample, and/or for aesthetic reasons.

Cover sheet 22 can be selected to provide the mount of oxygen transmission necessary for the type of microorganism desired to be grown. For example, polyester films have a low oxygen permeability (less than 0.78 $g/100$ $cm^2/24$ hours per 25μ of thickness), and would be suitable for growing anaerobic bacteria. On the other hand, some forms of polyethylene have a relatively high oxygen permeability (approximately 78 $g/100$ $cm^2/24$ hours per 25μ of thickness), and would be suitable for the growth of aerobic organisms, with or without the use of an air permeable membrane. One preferred material for cover sheet 22 is a 1.6 mil biaxially-oriented polypropylene film. Another preferred material for the cover sheet is a commercially available polyethylene terephthalate treated with an antifog agent (commercially available as FSI-47 from Film Specialties Inc., Whitehouse, N.J.). Another preferred material is sol-gel treated polyethylene terephthalate (commercially available as SCOTCHPAR brand film No. FE 40492 from 3M, St. Paul, Minn.). It is understood that cover sheet 22 can alternatively be affixed to body member 11. The cover sheet can be affixed by conventional methods such as heat sealing, adhesives, double coated adhesive tapes and the like.

Although both of the embodiments illustrated in FIGS. 1 and 3 have cover sheet 22 attached to culture media device 10, it is also contemplated within the scope of the invention that culture media devices 10 can be uncovered, and simply placed in a sterile environment during storage and incubation.

Insert Member

The test sample may be either an inoculum or a membrane such as a microbial filter. Various membranes and films can be used to provide the surface colonies of microorganisms to be grown, detected and/or enumerated by the method and devices of the invention. Particularly suitable are known microporous filters which have been commonly used to separate small microorganism populations, such as bacteria from large fluid samples. Such filters have previously been placed on the surface of agar media and incubated to allow counting and evaluation of the filtered microbes. Such filters have been available from such companies as Millipore Corp. Marlborough, Mass. and Gelman Corp., Ann Arbor, Mich. Millipore provides filters which are suitable such as the HAWG series, e.g., HAWG 04750 type HA. Gelman provides filters which are suitable such as the Metricel type, e.g., GN-6 Metricel membrane. Other suitable membranes include hydrophilic membranes prepared by providing coatings on various polymers comprising of homo- or copolymers of vinyl alcohol. This technology is described in International Application WO 92/07899. A vinyl alcohol coated microporous polypropylene prepared by the method described in Example 5 of the International Application is a preferred microorganism filter in the present invention.

Films of the microorganism filters described above are generally relatively thin, about 0.01–2 mm thick and preferably 0.05–1.0 mm thick, and may be provided in any desired 2 dimensional shape, e.g., as rectangles, as discs including partial discs and the like.

Microorganisms are separated by such filters with varying efficiency depending upon the sizes of the pores in the membranes. Bacteria are readily separated and yeasts and molds will also be separated by such filters. Filtration is carried out by conventional methods using funnels and discs of suitable sizes. Discs are preferably handled aseptically with tweezers. Discs may be made by the user from commercially available materials or are provided in aseptic packages as separate entities or as parts of kits of the invention.

Kits of the Invention

The kits provided by the invention include two or more parts. One part includes a thin film culture plate device Of the invention, which optionally include a cover sheet, which preferably covers all of the aperture of the culture plate device.

A second part of each kit may be one or more microbial filters of a shape and size suitable for fitting into the aperture of the spacer member of the culture plate device of the kit. Filters of different kinds can be provided with a kit, or multiple kits can contain various filters. The filters are optionally, and preferably provided in aseptic condition such as a polyethylene coated paper package which has been sterilized by gamma irradiation, ethylene oxide or other sterilization. Alternatively the filters may be unsterilized units which are to be sterilized by the user.

If the kit does not contain one or more microbial filters, it will contain a package of hydrophilic agents. Preferably both filters and packages will be provided in each kit. The hydrophilic agents are preferably contained in a sterile package for example a foil package such as those conventionally used in the pharmaceutical industry. An example of such a package is used for NITRO-BID Ointment (Marlon Laboratories, Inc., Kansas City, Mo.).

The nutrients and/or selective agents included in the packages are the same as those discussed earlier which may be incorporated into the adhesive compositions. The selection of the hydrophilic agents useful and necessary in the packages depends upon the microorganism to be evaluated. Another criteria for selection of components of a package will be short and long term chemical compatibility of the hydrophilic agents.

Inoculation Methods

Inoculation of the devices of the invention is carded out by one of several methods.

When no microbial filter is used, inoculation is carded out by including the hydrophilic agents in the cold-water-soluble powder adhered to the adhesive composition on the powder and adding an aqueous sample of microorganisms to be evaluated to the device through the aperture. Alteratively, inoculating the device with a sample contained in a membrane may be preceded by adding buffers, nutrients and/or selective agents provided by the user or provided from a sterile package, e.g., such as described for the kits of the invention.

When a microbial filter is used, the buffers, nutrients and/or selective agents are generally added to the device through the aperture before the filter, although the reverse order can be used. The buffers, nutrients and/or selective agents may be provided by the user or provided from a sterile package such as described for the kits of the invention.

The invention will be further illustrated by reference to the following non-limiting Examples. All parts and percentages are expressed as parts by weight unless otherwise indicated.

EXAMPLES

Example 1

One side of 0.13 mm thick polyethylene-coated paper (Schoeller Paper Inc., Pulaski, N.Y.) was coated with a noninhibitory adhesive copolymer of isooctyl acrylate (IOA) and acrylamide (ACM) at a 96:4 weight ratio (IOA:ACM) from a solution of about 20% solids in heptane/ethyl acetate (1:1) at a level (measured when dry) of about 0.9 mg/cm$^2$ and dried.

The adhesive was then dusted uniformly with a powder which was a mixture of 1 part by weight guar gum (Meyhall Chemical AG, Kreuzlingen, Switzerland) and 2 parts by weight of a xanthan gum (Kelco, Inc. San Diego, Calif.). This power-coated paper was disinfected by exposure to ethylene oxide.

A spacer was made from a rectangular (8 cm×11 cm) sheet of 0.08 in. (0.20 cm) thick polystyrene foam with a centered circular aperture (5 cm diameter) cut into it and attached by hand rolling pressure to a rectangular sheet of the above powder-coated paper.

A cover sheet was made from a stiff but flexible sheet of 4 mil (0.10 mm) thick sol-gel treated transparent polyester (SCOTCHPAR polyethylene terephthalate film, No. FE 40492, 3M, St. Paul, Minn.) in a rectangular shape (8 cm×11 cm). The cover sheet was attached to the 8 cm width of the edge of the foam of the device by double coated pressure sensitive tape on a 0.7 cm section of the cover sheet.

In use, the device was placed on a level surface and the top cover sheet folded back, exposing the foam spacer and the aperture therein. Into the aperture was added 1.0 ml of a buffered nutrient solution containing a selective agent (see Table 1). Over the solution and into the aperture was placed a 4.6 cm diameter disc of polyvinyl alcohol-treated hydrophilic polypropylene (prepared as described in published patent application WO 92/07899) that had been used to filter a 100 ml sample of liquid to remove the sample of known microorganisms. The cover sheet was then folded back down to cover the aperture without contacting the surface of the disc. The device was then incubated at 35° C. for 24 hours and examined to see if the bacteria detectable by the commercially available selective agent were present (and to count colonies if present).

TABLE I

| Microorganism | Nutrients | Results (cfu/ml) |
|---|---|---|
| coliform | M-Endo Agar | 221;230: ave. 226 |
| coliform | M-Endo broth, Ex. 1 device | 204;228: ave. 236 |
| mold | M-Green Agar | 160;180: ave. 170 |
| mold | M-Green broth, Ex. 1 device | 110;135: ave. 123 |
| yeast | M-Green Agar | 125 |
| yeast | M-Green broth, Ex. 1 device | 120;105: 113 |
| E. coli | M-FC Agar | 24;20: ave. 22 |
| E. coli | M-FC broth, Ex. 1 device | 23;27: ave. 25 |

Nutrients available from Difco, Inc., Detroit, MI

The results of these tests show that microorganisms detectable by the conventional (and cumbersome) agar plate method are readily detectable by the devices and method of this invention.

Example 2

One side of a 0.18 mm thick polyethylene terephthalate film was coated with a latex adhesive copolymer of isooctyl acrylate and N-vinylpyrrolidone reported in U.S. Pat. No. 5,232,838. The film was knife-coated with this adhesive composition at a level (measured when dried) of 6.2 mg/cm$^2$, and dried in an air oven at 93° C., to yield a sticky layer of the water-based adhesive composition on the surface of the substrate. The water-based adhesive composition was formed by dissolving 240 g of Endo nutrient formulation (BBL Inc., Baltimore, Md.) 10 g of agar gum (Hi-Tek Polymers Inc. of Louisville, Ky.) and 1 g agar (Difco, Inc. Detroit, Mich.) with stirring, in one liter of an emulsion suspension of the water-insoluble adhesive copolymer of isooctyl acrylate (IOA) and N-vinylpyrrolidone (NVP) at a 98:2 weight ratio (IOA:NVP). The components of the water-based adhesive copolymer included 1568 g of IOA (38.5 parts by weight), 32 g of NVP (0.8 parts), 2400 g of deionized water (59 parts), 68.8 g of IGEPAL CA89997 nonionic surfactant (1.7 parts), and 24 g of lauroyl peroxide (0.06 parts by weight).

A mixture of cold-water-soluble powders, formed of equal proportions by weight of xanthan gum (KELTROL, Kelco Inc., San Diego, Calif.) guar gum (Meyhall Chemical AG, Kreuzlingen, Switzerland) was dusted over the surface of the water-based adhesive layer. Any excess powder was shaken loose. This adhesive-coated and powder-coated paper was used to form the bottom portion of the thin film culture plate device.

A sheet of polystyrene foam with an aperture as in Example 1 was placed firmly over the powder coating. A cover sheet film of polyethylene terephthalate with an anti-fog treatment (FSI-47, Film Specialties Inc., Whitehouse, N.J.) was fitted to the polystyrene foam.

This thin film culture plate device was inoculated in the apertured space with 2 ml of a standard 0.1% M Peptone buffer. On top of the diluent was placed a 4.5 cm microorganism filter disc (HAWG 0450 type HA, Millipore Corp., Marlborough, Mass.) which had been used to filter a liquid sample of 100 ml. The filter disc spread, the buffer and the device was incubated at 37° C. for 24 hours and then checked for bacterial colonies on the surface of the filter and compare to a standard Endo agar petri dish culture plate. The results are shown in Table 2.

TABLE 2

|  | cfus/ml. | Green Metallic Sheen Colonies |
|---|---|---|
| Endo agar control | 78 | + |
| Ex. 2 device | 57 | + |

Example 3

In this example, river water samples were evaluated for the presence of bacteria. The devices used for evaluation of the river water samples were a standard commercially available aerobic count PETRIFILM culture plate device, standard R$_2$A (Acumedia, Baltimore, Mass.) agar petri dish culture plate and a device of the invention. 3 ml of river water is filtered through the treated polypropylene filter described in Example 1. The aerobic count PETRIFILM culture plate device was inoculated with 1 ml of R$_2$A broth and the filter is added. This filter process was repeated and a filter placed on R$_2$A agar. A third filter is inoculated onto the device of the invention. The results are shown in Table 3.

TABLE 3

|  | cfu's/ml for various water samples | | | |
|---|---|---|---|---|
|  | Apple River | | St. Croix River | |
| Device | 1 ml | 2 ml | 1.0 ml | 2.0 ml |
| PETRIFILM Ac device | 36 | 57 | 33 | 84 |
| R$_2$A agar with hydrophilic polypropylene filter* | 47 | 45 | 50 | 49 |
| Device of the invention (see Ex. 2) with hydrophilic polypropylene filter* | 45 | 62 | 51 | 63 |

*filter described in Example 1

These results show that the device of the invention successfully duplicates standard agar evaluations with greater convenience and lower cost.

Example 4

A culture plate device used in this example was constructed using a body member as described in Example 1 of U.S. Pat. No. 5,089,413, the disclosure of which is herein incorporated by reference. Briefly, a strip of microporous polyethylene membrane, 20.3 cm wide by 30.5 cm long and about 50 μm thick (porous polyethylene, available as ADVENT film product number 70-0000-4011-6, 3M, St. Paul, Minn.) was laminated by hand to the adhesive surface of a strip of polyethylene-backed pressure sensitive tape, 19.7 cm wide by 30.5 cm long, and 100 μm thick ("crepe" tape, product number 43-9100-5976-5, 3M, St. Paul, Minn.) to provide a substrate.

An adhesive solution to fix the medium to the substrate was made up as follows:

Three components, 5-bromo-4-chloro-3-indolylphosphate disodium salt (0.2 g), chloramphenicol (0.03 g), and chlortetracycline (0.03 g), were dissolved in methanol (40 ml). The resulting solution was added to a 100 ml of 48% (by weight) solution of copolymer of 2-methylbutylacrylate and acrylic acid in a mole ration of 90/10 (3M, Specialty Chemicals Division, St. Paul, Minn.) in 65/33 (v/v) heptane and acetone. The solution was stirred until it appeared homogeneous.

The adhesive solution was then coated on a surface of the substrate, using a lab knife coater, at a final dry coating weight of about 24.5 mg/100 cm². The coated substrate was allowed to dry in air.

A mixture of powdered nutrients and powdered gelling agent in a 1:4 ratio (by weight) was prepared. The nutrient was a powdered nutrient available from Acumedia Corp., Baltimore, Md.), 0.455 kg of which contains 200 g brain heart infusion, 200 g glucose, 54 g neopeptone, 1.0 g calcium chloride, and 0.2 g water. The gelling agent was a mixture (1:1 by weight) of xanthan gum (Kelco Co., San-Diego, Calif.) and locust bean gum (Hi-Tech Polymers, Inc., Louisville, Ky.). The nutrient and gelling agent powder mixture was sterilized with ethylene oxide, thoroughly aerated to remove all traces of residual sterilant, and screened to a size such that 90% passed through a 100-mesh screen. The powder mixture was fixed on the adhesive coating with a powder coater at a weight of about 40 mg/100 cm². This powder-coated article served as the body member of the device.

A spacer was made from a rectangular (8 cm×11 cm) sheet of 0.08 in. (0.20 cm) thick polystyrene foam with a centered circular aperture (5 cm diameter) cut into it and attached by hand rolling pressure to a rectangular sheet of the above powder-coated body member.

A cover means of the type used in Example 2 was provided of FSI-47 from Film Specialties, Inc. It covered the entire top of the device as shown in FIG. 1 and was assembled by placing a strip of double coated pressure sensitive tape (No. 1522 Double Coated Tape, 3M, St. Paul, Minn.) along the center of the body member's powdered surface, placing the cover means carefully over this, powder side down, and pressing the two sheets together by hand along the strip of double coated tape. The article thus obtained was cut with a scissors down the center of the strip of double coated tape. Each of the resulting two pieces was cut with a scissors at 7.6 cm intervals in order to obtain 8 devices, each of a size 7.6 cm by 10.2 cm.

The resultant devices were sterilized with gamma radiation (3 megarads) before use.

Two evaluations were carried out. For sample one, a 1.0 ml sample of molds was added directly through the aperture to the powder. For sample two, 1.0 ml of 1% peptone buffer was added to the powder through the aperture, then a duplicate sample of the 1.0 ml sample of molds was filtered through a 4.6 cm diameter disc of polyvinyl alcohol-treated polypropylene (as described in Example 1). The filter disc was then placed in the aperture of the device over the peptone buffer.

The devices were handled using normal sterile procedures. The cover sheet was folded to cover the aperture completely. The devices were incubated for 5 days at 25° C.

The results are shown in Table 4.

TABLE 4

| Mold | Sample 1 (cfu/ml) | Sample 2 (cfu/ml) |
| --- | --- | --- |
| M-19 | 119 | 107 |

These results demonstrate that both procedures provide comparable values for mold count.

What is claimed is:

1. A surface colony counting thin film culture plate device comprising:
    (a) a body member comprising a self-supporting substrate with upper and lower surfaces;
    (b) an adhesive composition coated on the upper surface of the substrate comprising a water-insoluble adhesive, a non-inhibitory emulsifying agent, and at least one hydrophilic agent selected from the group consisting of a nutrient for growing microorganisms, a selective agent, and combinations thereof;
    (c) cold-water-soluble powder comprising at least one gelling agent adhered to the composition, wherein addition of liquid to the composition and powder produces a hydrated gel on the surface of the substrate;
    (d) a cover sheet attached to the body member;
    (e) a water-insoluble spacer containing an aperture wherein the spacer has a thickness in the range of at least about 1.3 millimeters to about 2 millimeters such that the spacer prevents contact of the cover sheet with the hydrated gel and wherein the cover sheet covers the aperture; and
    (f) a membrane adapted to fit within the aperture of the spacer on the gel wherein the cover sheet does not contact the membrane when it is positioned within the aperture of the spacer on the gel such that the device is adapted to grow microorganisms on the surface of the hydrated gel.

2. The device of claim 1 wherein the cover sheet is a transparent cover sheet.

3. A kit for growing, detecting and/or enumerating microorganisms comprising a thin film culture plate device of claim 1, and packaged hydrophilic agents.

4. A method of using a surface colony counting culture media device to detect microorganisms in an aqueous test sample comprising:
    (a) adding an aqueous mixture comprising water and a hydrophilic agent to an aperture of a water-insoluble spacer of a surface colony counting culture media device wherein the surface colony counting culture media device comprises a body member, the body member comprising a self-supporting substrate with upper and lower surfaces; an adhesive composition coated on the surface of the substrate; a cold-water-soluble powder capable of forming a hydrated gel when exposed to the aqueous mixture, wherein the powder is adhered to the adhesive composition; a cover sheet affixed to the body member to cover the aperture; and wherein the spacer has a thickness in the range of at least about 1.3 millimeters to about 2 millimeters such that the spacer prevents contact of the cover sheet with the hydrated gel;
    (b) forming a hydrated gel;
    (c) inserting a membrane which has been used to filter a liquid sample to be evaluated for the presence of microorganisms into the aperture space onto the aqueous mixture;

(d) covering the aperture space with the cover sheet wherein the cover sheet does not contact the membrane positioned within the aperture;
(e) incubating the device for a period of time; and
(f) counting the number of microorganism colonies growing on the surface of the membrane filter.

5. The method of claim 4 wherein the hydrophilic agent is at least one selective agent.

6. The method of claim 5 wherein a liquid sample is added in step (a) and use of a membrane is optional.

* * * * *

UNITED STATES PATENT AND TRADEMARK OFFICE
CERTIFICATE OF CORRECTION

PATENT NO.: 5,681,712

DATED: October 28, 1997

INVENTOR(S): Robert L. Nelson

It is certified that error appears in the above-identified patent and that said Letters Patent is hereby corrected as shown below:

Column 10, line 21: Delete the word "carded" and insert in place thereof--carried--.

Column 10, line 23: Delete the word "carded" and insert in place thereof--carried--.

Claim 1, column 14, line 23: Before the word "composition" insert the word --adhesive--.

Signed and Sealed this

Eighteenth Day of May, 1999

Attest:

Q. TODD DICKINSON

Attesting Officer

Acting Commissioner of Patents and Trademarks